US006462097B1

(12) United States Patent
Martino et al.

(10) Patent No.: US 6,462,097 B1
(45) Date of Patent: Oct. 8, 2002

(54) PROCESS FOR THE PRODUCTION OF PURIFIED WATER AND HYDROCARBONS FROM FOSSIL RESOURCES

(75) Inventors: Germain Martino, Poissy (FR); Philippe Courty, Villejuif (FR); Pierpaulo Garibaldi, Peschiera Borromeo (IT)

(73) Assignees: Institut Francais Du Petrole, Rueil-Malmaison Cedex; Agip Petroli S.p.A., Rome (IT); Eni S.p.A., Rome (IT)

( * ) Notice: Subject to any disclaimer, the term of this patent is extended or adjusted under 35 U.S.C. 154(b) by 0 days.

(21) Appl. No.: 09/822,409

(22) Filed: Apr. 2, 2001

(30) Foreign Application Priority Data

Mar. 31, 2000 (FR) ............................................ 00 04131

(51) Int. Cl.[7] ........................ C07C 27/00; B01D 33/70; B01D 15/00; C02F 3/02; B01J 49/00
(52) U.S. Cl. ........................ 518/700; 210/150; 210/620; 210/660; 210/670
(58) Field of Search .......................... 518/700; 210/150, 210/620, 660, 670

(56) References Cited

U.S. PATENT DOCUMENTS

| 4,046,831 | | 9/1977 | Kuo ...................... 260/676 R |
| 4,049,741 | | 9/1977 | Kuo et al. .............. 260/676 R |
| 4,513,156 | | 4/1985 | Tabak ......................... 585/329 |
| 4,585,063 | * | 4/1986 | Venardos et al. ........... 166/259 |
| 5,429,942 | | 7/1995 | Kock et al. .................... 435/64 |
| 6,225,358 | * | 5/2001 | Kennedy et al. ............. 518/700 |

FOREIGN PATENT DOCUMENTS

| EP | 0 839 892 A2 | 5/1998 |
| EP | 0 901 805 A1 | 3/1999 |
| WO | WO84/04913 | 12/1984 |

* cited by examiner

*Primary Examiner*—Jafar Parsa
(74) *Attorney, Agent, or Firm*—Millen, White, Zelano & Branigan, P.C.

(57) ABSTRACT

A process for the production of purified water and hydrocarbons comprising at least one stage of separation of the water and hydrocarbons formed during a Fischer-Tropsch synthesis, at least one stage of purification of the separated water by bringing it into contact with at least one adsorbent selected from the group consisting of: the active carbons, clays which are hydrophobic or rendered hydrophobic, and zeolites which are hydrophobic or rendered hydrophobic. This process may optionally include a stripping stage before the adsorption step.

15 Claims, 1 Drawing Sheet

PROCESS FOR THE PRODUCTION OF PURIFIED WATER AND HYDROCARBONS FROM FOSSIL RESOURCES

The present invention concerns a process for the production of purified water and hydrocarbons from Fischer-Tropsch synthesis. This process makes it possible to eliminate the impurities present in the water produced during this synthesis, in particular water-soluble oxygenated compounds, as well as the metals generally produced by the catalyst used in the synthesis stage.

PRIOR ART

The Fischer-Tropsch synthesis is a process which simultaneously produces water and hydrocarbons. For example when the fossil resource under consideration is natural gas mainly constituted by methane, the global reaction can be written:

$$nCH_4 + n/2\ O_2 \rightarrow n(-CH_2-) + n\ H_2O \tag{1}$$

The quantities of water co-produced are considerable. Thus an industrial unit producing 500,000 t distillates per year co-produces approximately 600,000 t water per year, i.e. approximately one barrel of water per barrel of hydrocarbons.

Fischer-Tropsch synthesis consists, in an initial stage, of transforming the fossil resource (for example natural gas, or a naphtha cut or a heavy petroleum cut, or coal) into synthesis gas, i.e. into a gaseous mixture containing carbon monoxide, carbon dioxide and hydrogen.

In the case of natural gas, gas production processes are generally used which involve synthesis by partial oxidation or steam reforming, or else by a combination of the two aforementioned technologies. When the fossil resource is coal, lignite, asphalts or residues of petroleum origin, gasification or partial oxidation processes are used to produce the synthesis gas.

In a second stage the synthesis gas is converted into water and hydrocarbons according to the reaction:

$$nCO + 2n\ H_2 \rightarrow n(-CH_2-) + n\ H_2O \tag{2}$$

It is known that this reaction, which is strongly exothermic, is generally carried out in the presence of catalysts essentially comprising the metals iron or cobalt deposited on a support phase based on metal oxides such as aluminium, silicon or titanium oxide. Said catalysts are used in various types of reactors, for example multi-tubular isothermal reactors or fluidised bed reactors. In a preferred process, the said catalysts are used in suspension in a liquid phase made up of hydrocarbons ("slurry" technology).

In a third stage the hydrocarbons formed are converted partly by means of a hydro-isomerising hydro-cracking process carried out in the presence of a catalyst. Liquid hydrocarbon cuts, for example medium distillates, oils and gases are obtained, which contain slightly isomerised products to improve their properties during use: flow point for the gas-oil and kerosene cuts, viscosity index for lubricants.

The water co-produced with the hydrocarbons is partly recycled in the synthesis gas production section, in particular when the said synthesis gas is produced by steam-reforming, and partly rejected following sufficient treatments to bring it up to standard (e.g. conformity to the chemical oxygen demand). The expert knows that said water contains numerous water-soluble oxygenated compounds (e.g. alcohols, aldehydes, ketones, acids, esters, acetates, aldols etc.), traces of hydrocarbons as well as traces of heavy metals from the catalyst (e.g. from the iron or cobalt) in concentrations generally ranging from 10 parts per million (ppm) to 0.001 ppm. The oxygenated compounds and the metals present in this water give it an odour, a taste, and a potential toxicity incompatible with use for sanitary purposes or for consumption.

Apart from water, the Fischer-Tropsch process co-produces carbon dioxide (CO2) in a fairly large quantity. The CO2 co-produced, apart from that originating from the oven combustion gases, comes from the synthesis gas generation stage and the Fischer-Tropsch synthesis itself (reaction 2 above) and the carbon dioxide conversion reaction (Water Gas Shift, reaction 3 below), whose degree of advance depends in particular on the nature of the catalyst used for the hydrocarbon synthesis (reaction 2).

$$m\ CO + m\ H_2O \rightarrow m\ CO_2 + m\ H_2 \tag{3}$$

Part of the CO2 can be recycled to the synthesis gas production unit but, overall, all the oxygen present in the synthesis gas is found in the form of water or CO2 in the reaction products.

The expert also knows that the used waters can be effectively purified by a series of processes, some of which use adsorption on solids, and others biodegradation on dedicated strains of bacteria. The patent U.S. Pat. No. 5,569,790 describes a process for the purification of water used for washing a hydrocarbon charge involved in an ether production process. This purification is carried out by means of liquid-liquid contact with an amount of effluent arising from an etherification unit. In this process, the degree of purification of the water is limited, as the division of the impurities is carried out in favour of the aqueous phase. Moreover, such a process does not enable metals to be eliminated correctly.

The patent FR-2.772.373 describes a process for purification of a fluid, and in particular a process for the elimination of polar compounds contained in the washing water produced by an etherification unit. This process consists of bringing the fluid to be purified into contact with a vapour phase, to get rid of the majority of the impurities. The purification can be carried out by passing the fluid over a solid phase chosen to retain the impurities. The possibility of eliminating the oxygenated compounds and the metals simultaneously is neither described nor mentioned in this application.

SUMMARY OF THE INVENTION

The invention concerns a process for the production of purified water and hydrocarbons resulting from Fischer-Tropsch synthesis, comprising at least one stage of separation of the water and hydrocarbons formed during the Fischer-Tropsch synthesis, at least one stage of purification of the separated water by means of contact with at least one adsorbent selected from the group consisting of: the active carbons, clays which are hydrophobic or rendered hydrophobic, and zeolites which are hydrophobic or rendered hydrophobic. This process may in addition include a stripping stage before the purification by adsorption.

DETAILED DESCRIPTION OF THE INVENTION

It has been found that by means of a simple technique involving adsorption on solids, it is possible to simultaneously eliminate oxygenated compounds, hydrocarbons and also the heavy metals present in the water co-produced with the hydrocarbons in the Fischer-Tropsch synthesis and thus to confer upon it usage properties compatible with use for sanitary purposes and, preferably for consumption.

It has also been found that water for consumption thus produced can possibly, after adjustment of its mineralisation, be gasified, partly using the CO2 resulting from at least one of the stages of the Fischer-Tropsch process.

The process according to the invention consists of separating the water formed from the hydrocarbons co-produced in the Fischer-Tropsch synthesis, possibly condensing this water after separation, then purifying said water by bringing it into contact with at least one adsorbent, selected from the group consisting of: the active carbons, clays which are hydrophobic or rendered hydrophobic, and zeolites which are hydrophobic or rendered hydrophobic. The clays or zeolites can be rendered hydrophobic by any means known to a man skilled in the art, e.g. by silicon grafting or dealumination.

The adsorbent according to the invention is preferably selected from the group consisting of: dealuminated zeolites with an Si/Al atomic ratio greater than or equal to ca. 20, silicalite, and clays which are hydrophobic or rendered hydrophobic. In a more preferred process the dealuminated zeolites in this group are either at least one dealuminated ZSM-5 zeolite, or at least one dealuminated Y zeolite, or a mixture of these two types of zeolite. In a highly preferred process, the adsorbent is a ZSM-5 zeolite with an Si/Al atomic ratio greater than or equal to ca. 20 or a dealuminated Y zeolite with an Si/Al atomic ratio greater than or equal to ca. 20 or a mixture of these zeolites with an Si/Al atomic ratio greater than or equal to ca. 20. Such an adsorbent makes it possible to simultaneously eliminate the different types of impurity contained in the water resulting from the Fischer-Tropsch synthesis, i.e. in particular oxygenated compounds and heavy metals.

When the adsorbent is a zeolite, it is in fact preferable for its Si/Al atomic ratio to be greater than or equal to ca. 20, more preferable for it to be greater than or equal to ca. 50, and highly preferable for it to be greater than or equal to ca. 100.

The adsorption stage is carried out by bringing the water into contact with the adsorbent placed in a reactor. Any type of reactor known to the expert can be used. The adsorption is generally effected at a temperature below ca. 50° C., more preferably below ca. 40° C., and highly preferably below ca. 30° C., and especially preferably below ca. 25° C. The mass of water treated per unit of mass of adsorbent and per hour is generally at least equal to approximately 5 $h^{-1}$, preferably generally less than approximately 3 $h^{-1}$, and highly preferably less than 1 $h^{-1}$.

Having reached saturation of said adsorption mass, the flux of water to be purified may be guided towards a second reactor and the saturated adsorbent may be regenerated by any technique known to a man skilled in the art, for example by stripping with water vapour at a temperature of at least 110° C., preferably 130° C., and highly preferably 150° C., so as to reduce the adsorbate content of said mass at least down to 1%, and preferably less than 0.5% of the mass.

Moreover, unexpectedly, the gaseous flow obtained during stripping with water vapour and containing the aforementioned impurities can be converted into hydrocarbons which can be further utilised. This is preferentially achieved by recycling all or part of the said flux towards the synthesis gas production section necessary for the hydrocarbon production stage.

According to a preferred method for implementing the procedure according to the invention, another stage of purification can be effected before the water purification treatment by adsorption. This stage consists of partially purifying the said water by stripping under a pressure preferably between 0.02 and 10 MPa, preferably with an inert gas or medium-pressure water vapour, i.e. water vapour or an inert gas at a pressure generally above 0.02 MPa and below 10 MPa, more preferably between 0.02 MPa and 5 MPa, and highly preferably between 0.02 MPa and 3 MPa. This water vapour or inert gas are used at a temperature generally within the range 60° C. to 210° C., preferably within the range 80° C. to 200° C. and more preferably close to 150° C., with a water vapour or inert gas to liquid water ratio in terms of mass preferably above or equal to 10, more preferably above or equal to 7, and highly preferably above or equal to 5, for a period sufficient to eliminate at least 30%, preferably at least 50%, highly preferably at least 70% and particularly preferably at least 80% of the aforementioned organic impurities.

It may be possible to inject at the stripping stage a dilute alkali or acid to maintain the pH within an approximately neutral range. The flux of vapour produced by the stripping may also be advantageously recycled to the synthesis gas production section.

After treatment of the impure water by adsorption and possibly pretreatment by stripping, it may be advantageous to post-treat the purified water by means of at least one biological process, e.g. by percolation on a bacterial bed and/or treatment on activated sludge according to technologies known to the man skilled in the art.

The purified water produced by means of the process according to the invention can be used, depending on its degree of purification, either for irrigation of dry geographical area, or for sanitary use, or for consumption.

When used for consumption, the water purified by means of the process according to the invention can advantageously be brought into contact with air, by means of any known process. It can also be advantageously mineralised, for example by the addition of carbonates, hydrogenocarbonates, sulphates, chlorides, phosphates, and metals selected from the group consisting of sodium, potassium, calcium and magnesium, without this list being exhaustive, in proportions known to the man skilled in the art.

Finally, the purified water, preferably drinkable, produced by means of the process according to the invention may possibly be gasified by being brought into contact, under slight pressure (preferably below 0.5 MPa) with part of the CO2 co-produced and purified in advance, in particular to remove the carbon monoxide, by any process known to the man skilled in the art.

BRIEF DESCRIPTION OF DRAWING

One of the preferred ways of implementing the process according to the invention is detailed in FIG. 1.

It consists, for example, of initially separating the water and the hydrocarbons formed during Fischer-Tropsch synthesis by a process known to the man skilled in the art, e.g. settling. The water to be purified, which is full of impurities such as polar compounds, possibly residual hydrocarbons and metals, is then sent via a pipe 1 by means of a pump 2, and after passing into a heat exchanger 3, into a purification column 4. It is for example introduced into the head of the purification column 4, via a pipe 5.

Figure 1:
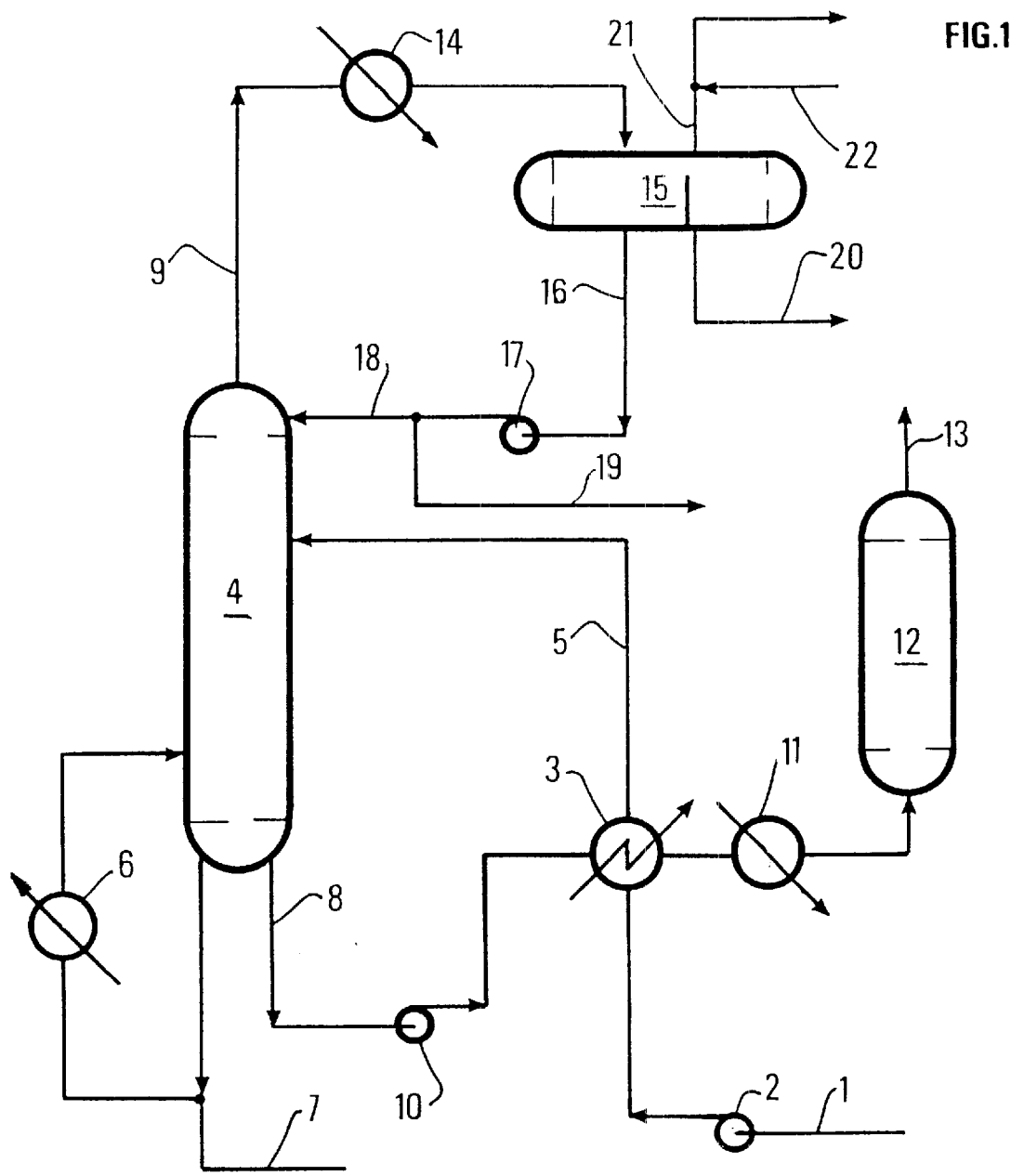

This purification column 4 has, in its lower section, a reboiler 6 whose function is in particular to initiate a vapour flux, by partial vaporisation of liquid. A liquid having a temperature sufficient to partially vaporise the liquid from the base of the column feeds the boiler 6. The pH value of the liquid at the base of the column can be controlled by automatic addition of dilute acid or alkali, added via a pipe 7.

The water, cleaned of part of its impurities, essentially of part of the water-soluble oxygenated compounds, is extracted from the base of the purification column 4 via a pipe 8, and the vapour phase which is full of impurities during the counter-current circulation is evacuated at the head of the column via a pipe 9.

The partially purified water extracted via the pipe 8 is taken up by a pump 10 and sent towards the heat exchanger 3 where it exchanges calories to reheat the washing water which is full of impurities, coming from pump 2. The partially purified water is then cooled in an exchanger 11 before being introduced into the adsorption device 12 which allows its purification to be completed. The purified water coming from the device 12 is extracted via a pipe 13.

The device 12 is made of an enclosure comprising at least one adsorbent, for example a hydrophobic dealuminated zeolite, whose special feature is to retain all the residual impurities (i.e. the metals, the oxygenated compounds and the hydrocarbons which were not eliminated during the stripping).

The vapour phase, full of impurities, evacuated via the pipe 9 is sent, via a condenser 14, into a reservoir 15 where it is separated into several effluents:

An essentially aqueous phase containing some of the impurities is evacuated via a pipe 16 at the base of the reservoir 15. This phase is taken up by a pump 17. A first part of this aqueous phase is sent via a pipe 18 to serve as reflux in the purification column 4, whilst a second part is sent via a purge line 19 so as to eliminate part of the impurities. This second part 19 can be recycled to a synthesis gas production unit to make use of the water and the organic compounds which it contains.

An organic phase may possibly be evacuated from the reservoir 15 via a pipe 20.

A gaseous phase or gaseous purge containing hydrocarbons and impurities evacuated at the head of the reservoir via a conduit 21.

In the case of there being no gaseous purge, a pipe 22 connected to the pipe 21 enables a certain quantity of nitrogen to be introduced to maintain a given pressure inside the reservoir.

The rate of elimination of the impurities in the water resulting from the Fischer-Tropsch synthesis during implementation of the process according to the invention is generally above 85%. It is adjusted in accordance with the use intented for the purified water: irrigation of dry areas, or use as drinking water for example. Thus, in some cases, the rate of elimination of the impurities will preferably be greater than 90%, more preferably greater than 95%, and highly preferably close or equal to 100%. As regards metallic impurities present in the water to be purified, their rate of elimination will preferably be greater than 95%, more preferably greater than 98%, highly preferably close or equal to 99%, and even in certain cases greater than 99.5%.

To limit the consumption of utilities (condenser, heat exchangers etc.) thermal integration will, for example, be used. Thermal integration means the possibility of using hot or cold liquids resulting from the Fischer-Tropsch unit to serve as a heating agent at the reboiler 6, or cooling agent for the condenser 14 and/or the refrigeration exchanger 11.

In conclusion, the process according to the invention is a process for producing purified water and hydrocarbons comprising at least one stage of separation of the water and the hydrocarbons formed during Fischer-Tropsch synthesis, at least one stage of purification of the water separated, by means of contact with at least one adsorbent selected from the group consisting of: the active carbons, clays which are hydrophobic or rendered hydrophobic, and zeolites which are hydrophobic or rendered hydrophobic. The adsorbent used in the process according to the invention will preferably be selected from the group consisting of: dealuminated zeolites with an Si/Al atomic ratio greater than or equal to ca. 20, clays which are hydrophobic or rendered hydrophobic and silicalite.

The process according to the invention may further include, a stripping stage using water vapour or inert gas, before the purification-by-adsorption phase. The stripping is preferably effected under pressure between 0.02 and 10 MPa, at a temperature of between 60° C. and 100° C., and a water vapour or inert gas ratio to liquid water in terms of mass greater than or equal to 10.

The process according to the invention may further include, following the adsorption stage, a stage of treatment by at least one biological process, e.g. by percolation on a bacterial bed and/or treatment on activated sludge. It may also include, moreover, following the purification stage or stages, a stage bringing it into contact with air, and/or a stage of mineralisation of the purified water.

The process according to the invention may also include, moreover, following the mineralisation stage, a stage involving gasification under pressure lower than 0.5 MPa by means of the carbon dioxide produced in the Fischer-Tropsch synthesis and purified.

In the process according to the invention, adsorption is preferably performed at a temperature below ca. 50° C., and the mass of water treated per unit of mass of adsorbent and per hour is at the most equal to ca. $5h^{-1}$.

In the process according to the invention, the adsorption stage can also possibly be achieved by at least 2 reactors: at least one reactor performing adsorption and at least one other reactor allowing regeneration of an adsorption mass, which was previously saturated.

The following example illustrates one possible way to carry out the invention.

EXAMPLE

The Fischer-Tropsch reaction is operated continuously in a reactor consisting in a bubble column operated under a three phase regime, with a diameter of 50 mm and a height of 1500 mm.

This column is equipped with an injection nozzle for synthesis gas at the bottom of the column, a nozzle for drawing off the suspension above the liquid level, a nozzle for re-injection of the suspension at the bottom of the column, and a recirculating loop comprising a degasifier, a pump and a decanter, to separate the catalyst from the liquid reaction products.

The catalyst is based on cobalt deposited on alumina, shaped as particles of 30–100 microns. It is introduced in the column, in an amount of 400 g, together with 1500 ml of nC18 paraffin. Synthesis gas (H2/CO=2) is introduced at a rate of 1 Nm3/h and the reaction is driven at P=2 MPa and T=230° C.

Under steady running conditions, the conversion is 60%. Reaction products are constituted by gaseous hydrocarbons (C1–C4, 24 kg/h), liquids (C5+, 56 kg/h) and water (103 kg/h).

Water is separated by decantation of liquid hydrocarbons. It contains alcohols, organic acids and ketones, under the proportions given hereunder:

| | |
|---|---|
| methanol | 0.380 weight % |
| ethanol | 0.240 |
| propanol | 0.080 |
| butanol | 0.046 |
| pentanol | 0.029 |
| hexanol and higher alcohols | 0.043 |
| acetone | 0.002 |
| acetic acid | 0.044 |
| propionic acid | 0.020 |
| butanoic acid | 0.007 |
| dissolved hydrocarbons | 0.050 |

The BOD (Biological Oxygen Demand) and COD (Chemical Oxygen Demand) of this effluent are respectively 10 570 and 15 400 mg/l O2. This effluent is submitted to a stripping by low pressure steam (0.4 MPa, 150° C., steam/water=2/1 weight/weight) in a packed column of a diameter of 50 mm and a height of 500 mm, this has the effect of reducing the content in light alcohols and ketones which becomes:

| | |
|---|---|
| methanol: | 0.080 weight % |
| ethanol: | 0.060 |
| propanol | 0.040 |
| acetone | 0.001 | without modifying the content in other oxygenated compounds.

The stripped effluent is sent to the top of a column of a diameter of 25 mm and a height of 80 mm containing a bed of Wessalith DAY (DEGUSSA), at 25° C. and pph=1 h−1. At the outlet of this step, the content in C1–C8 alcohols and inorganic acids is lower than 0.005 weight %, and the content in hydrocarbons lower than 0.001 weight %. The BOD and COD of this effluent are lower than 100 mg/l O2.

After saturation of the adsorbant by organic products, mainly alcohols, which takes place after 100 hours on stream, the latter is regenerated by stripping under a nitrogen stream at 300° C. The adsorption capacity of the solid decreases slightly but regularly along the cycles.

Regeneration by calcination under air at 500° C. is performed after 1000 hours on stream, under the conditions indicated hereunder, so as to eliminate traces of oxygenated compounds which are not desorbed by the nitrogen stream. The adsorption capacity is totally recovered through this treatment.

This example shows that the effluent has been cleared from its main organic impurities through stripping and adsorption on a specific adsorbent. After pH adjustment, it can be released in the sea. After adjustment of pH and a light biological treatment, it can be employed for sanitary uses.

What is claimed is:

1. A process for producing purified water and hydrocarbons comprising conducting at least one stage of separation of water and hydrocarbons formed during a Fischer-Tropsch synthesis, and conducting at least one purification of the separated water, comprising pre-treating said water with a stripping stage including injecting a dilute alkali or acid to maintain an approximately neutral pH, contacting the separated water, in at least one adsorption stage, with at least one adsorbent selected from the group consisting of: active carbons, hydrophobic clays and hydrophobic zeolites and wherein said purified water can be used for sanitary or irrigation use and consumption.

2. A process according to claim 1, wherein the adsorbent comprises: a dealuminated zeolite with an Si/Al atomic ratio greater than or equal to 20, a hydrophobic clay or silicalite.

3. A process according to claim 1, further comprising upstream of the adsorption stage, subjecting the separated water to a stripping stage with water vapour or an inert gas.

4. A process according to claim 3, wherein the stripping stage is conducted under a pressure of between 0.02 and 10 MPa, at a temperature of between 60° C. and 210° C., and a water vapour or inert gas to liquid water in a ratio, in terms of mass, greater than or equal to 10.

5. A process according to claim 1, further comprising, after the adsorption phase, subjecting the resultant water to a stage of treatment by at least one biological water treatment process.

6. A process according to claim 4, further comprising aerating the water after the final purification stage.

7. A process according to claim 6, further comprising a mineralization stage after the final purification stage comprising adding minerals to the purified water.

8. A process according to claim 7, further comprising, after the mineralization stage, subjecting the water to a gasification stage under a pressure of less than 0.5 MPa with carbon dioxide.

9. A process according to claim 1, wherein the adsorption stage is performed at a temperature about below 50° C., and the mass of water treated per unit of mass of adsorbent and per hour is at the most equal to about 5 h−.

10. A process according to claim 1, wherein the adsorption stage comprises at least 2 reactors: performing adsorption in at least one reactor and regenerating at least one other reactor of an adsorption mass which was previously saturated in another reactor.

11. A process according to claim 5, wherein the biological water treatment process is conducted on a bacterial bed.

12. A process according to claim 5, wherein the biological water treatment process is conducted in an activated sludge process.

13. A process according to claim 1, further comprising conducting a Fischer-Tropsch synthesis upstream of said separation stage so as to provide said water and hydrocarbons.

14. A process according to claim 8, further comprising conducting a Fischer-Tropsch synthesis upstream of said separation stage so as to provide said water and hydrocarbons and said $CO_2$.

15. A process according to claim 1, wherein the adsorbent comprises: a dealuminated zeolite with an Si/Al atomic ratio greater than or equal to 50, a hydrophobic clay or silicalite.

* * * * *

UNITED STATES PATENT AND TRADEMARK OFFICE
CERTIFICATE OF CORRECTION

PATENT NO.   : 6,462,097 B1
DATED        : October 9, 2002
INVENTOR(S)  : Martino et al It is certified that error appears in the above-identified patent and that said Letters Patent is hereby corrected as shown below:

<u>Column 8,</u>
Line 37, change "5h" to -- $5h^{-1}$ --.

Signed and Sealed this

First Day of July, 2003

JAMES E. ROGAN
*Director of the United States Patent and Trademark Office*